(12) United States Patent
Pélissier et al.

(10) Patent No.: US 8,298,290 B2
(45) Date of Patent: Oct. 30, 2012

(54) IMPLANTABLE PROSTHESIS FOR SOFT TISSUE REPAIR

(75) Inventors: Edouard Pélissier, Devecey (FR);
Valerie L. Vadurro, Warwick, RI (US);
Stephen T. Clarke, Portsmouth, RI (US); Roger E. Darois, Foster, RI (US);
David W. Hass, West Greenwich, RI (US)

(73) Assignee: Davol, Inc., Warwick, RI (US)

( * ) Notice: Subject to any disclaimer, the term of this patent is extended or adjusted under 35 U.S.C. 154(b) by 1000 days.

(21) Appl. No.: 10/945,532

(22) Filed: Sep. 20, 2004

(65) Prior Publication Data

US 2006/0064175 A1 Mar. 23, 2006

(51) Int. Cl.
*A61F 2/02* (2006.01)
(52) U.S. Cl. .................................... 623/23.72; 606/151
(58) Field of Classification Search .... 623/23.72–23.74; 606/151, 213
See application file for complete search history.

(56) References Cited

U.S. PATENT DOCUMENTS

| | | | |
|---|---|---|---|
| 2,671,444 A * | 3/1954 | Pease, Jr. | 606/151 |
| 3,463,158 A | 8/1969 | Schmitt et al. | |
| 3,739,773 A | 6/1973 | Schmitt et al. | |
| 3,875,937 A | 4/1975 | Schmitt et al. | |
| 4,561,434 A | 12/1985 | Taylor | |
| 4,693,720 A | 9/1987 | Scharnberg et al. | |
| 4,710,192 A | 12/1987 | Liotta et al. | |

(Continued)

FOREIGN PATENT DOCUMENTS

| | | |
|---|---|---|
| EP | 0 827 724 A2 | 3/1998 |
| EP | 0 537 769 B1 | 4/1998 |
| FR | 2 719 993 A1 | 11/1995 |

(Continued)

OTHER PUBLICATIONS

English translation of Notice of Reasons for Rejection, dated Jun. 23, 2011, for Japanese Patent Application No. 2007-532550 (4 pages).

*Primary Examiner* — Gary Jackson
*Assistant Examiner* — Eric Blatt
(74) *Attorney, Agent, or Firm* — Wolf, Greenfield & Sacks, P.C.

(57) ABSTRACT

An implantable prosthesis for repairing or augmenting anatomical defects, including an inguinal hernia. The prosthesis includes a repair fabric having a body portion and a support member that may be arranged in or on the repair fabric to help deploy the repair fabric at the surgical site and/or help inhibit folding or buckling of the repair fabric. The support member may substantially surround the body portion to help deploy and/or hold the body portion in a spread out configuration for covering the defect. The support member may include first and second ends that are spaced apart to form an interruption so that a slit or keyhole arrangement may be formed in the repair fabric through the interruption and into an interior region of the body portion to receive a body structure, including a cord structure such as the spermatic cord. A portion of the support member may deviate inwardly toward the body portion to form an indentation that is adapted to be positioned adjacent to a body structure, such as the femoral vessels during an inguinal hernia repair procedure. The indentation may be offset to one side of the prosthesis. The support member and/or the repair fabric may be configured so as to inhibit protrusion of the ends of the support member through the fabric in the vicinity of the interruption. The support member may be formed of a monofilament comprised of a non-resorbable or resorbable material.

24 Claims, 3 Drawing Sheets

U.S. PATENT DOCUMENTS

| | | | |
|---|---|---|---|
| 4,796,603 | A | 1/1989 | Dahlke et al. |
| 4,840,626 | A | 6/1989 | Linsky et al. |
| 4,865,026 | A | 9/1989 | Barrett |
| 4,892,541 | A | 1/1990 | Alonso |
| 5,002,551 | A | 3/1991 | Linsky |
| 5,007,916 | A | 4/1991 | Linsky et al. |
| 5,032,445 | A | 7/1991 | Scantlebury et al. |
| 5,116,357 | A | 5/1992 | Eberbach |
| 5,122,155 | A | 6/1992 | Eberbach |
| 5,141,515 | A | 8/1992 | Eberbach |
| 5,147,374 | A | 9/1992 | Fernandez |
| 5,163,954 | A | 11/1992 | Curcio et al. |
| 5,254,133 | A | 10/1993 | Seid |
| 5,258,000 | A | 11/1993 | Gianturco |
| 5,290,217 | A | 3/1994 | Campos |
| 5,292,328 | A | 3/1994 | Hain et al. |
| 5,334,217 | A | 8/1994 | Das |
| 5,350,399 | A | 9/1994 | Erlebacher et al. |
| 5,356,432 | A | 10/1994 | Rutkow et al. |
| 5,366,460 | A | 11/1994 | Eberbach |
| 5,368,602 | A | 11/1994 | de la Torre |
| 5,397,331 | A | 3/1995 | Himpens et al. |
| 5,433,996 | A | 7/1995 | Kranzler et al. |
| 5,456,720 | A | 10/1995 | Schultz et al. |
| 5,507,811 | A | 4/1996 | Koike et al. |
| 5,578,045 | A | 11/1996 | Das |
| 5,593,441 | A | 1/1997 | Lichtenstein et al. |
| 5,634,931 | A | 6/1997 | Kugel |
| 5,681,342 | A | 10/1997 | Benchetrit |
| 5,695,525 | A | 12/1997 | Mulhauser et al. |
| 5,697,978 | A | 12/1997 | Sgro |
| 5,702,416 | A | 12/1997 | Kieturakis et al. |
| 5,716,408 | A | 2/1998 | Eldridge et al. |
| 5,716,409 | A | 2/1998 | Debbas |
| 5,725,577 | A | 3/1998 | Saxon |
| 5,743,917 | A | 4/1998 | Saxon |
| 5,766,246 | A | 6/1998 | Mulhauser |
| 5,769,864 | A | 6/1998 | Kugel |
| 5,813,975 | A | 9/1998 | Valenti |
| 5,824,082 | A * | 10/1998 | Brown ........................ 623/11.11 |
| 5,836,961 | A | 11/1998 | Kieturakis et al. |
| 5,857,467 | A * | 1/1999 | Faries et al. ................... 128/849 |
| 5,876,447 | A | 3/1999 | Arnett |
| 5,879,366 | A | 3/1999 | Shaw et al. |
| 5,916,225 | A | 6/1999 | Kugel |
| 5,919,232 | A | 7/1999 | Chaffringeon et al. |
| 5,922,026 | A | 7/1999 | Chin |
| D416,327 | S | 11/1999 | Kugel |
| 6,066,777 | A | 5/2000 | Benchetrit |
| 6,077,281 | A | 6/2000 | Das |
| 6,080,182 | A | 6/2000 | Shaw et al. |
| 6,090,116 | A | 7/2000 | D'Aversa et al. |
| 6,113,623 | A | 9/2000 | Sgro |
| 6,113,624 | A | 9/2000 | Bezwada et al. |
| 6,162,962 | A | 12/2000 | Hinsch et al. |
| 6,166,286 | A | 12/2000 | Trabucco |
| 6,171,318 | B1 | 1/2001 | Kugel et al. |
| 6,174,320 | B1 * | 1/2001 | Kugel et al. ................... 606/151 |
| 6,176,863 | B1 | 1/2001 | Kugel et al. |
| 6,210,439 | B1 | 4/2001 | Firmin et al. |
| 6,214,020 | B1 | 4/2001 | Mulhauser et al. |
| 6,224,616 | B1 | 5/2001 | Kugel |
| 6,235,869 | B1 | 5/2001 | Roby et al. |
| 6,241,768 | B1 | 6/2001 | Agarwal et al. |
| 6,258,122 | B1 | 7/2001 | Tweden et al. |
| 6,258,124 | B1 | 7/2001 | Darois et al. |
| 6,267,772 | B1 | 7/2001 | Mulhauser et al. |
| 6,280,453 | B1 | 8/2001 | Kugel et al. |
| 6,287,316 | B1 | 9/2001 | Agarwal et al. |
| 6,290,708 | B1 | 9/2001 | Kugel et al. |
| 6,391,060 | B1 | 5/2002 | Ory et al. |
| 6,436,030 | B2 | 8/2002 | Rehil |
| 6,497,650 | B1 | 12/2002 | Nicolo |
| 6,517,576 | B2 | 2/2003 | Gabbay |
| 6,544,167 | B2 | 4/2003 | Buckberg et al. |
| 6,575,988 | B2 | 6/2003 | Rousseau |
| 6,610,006 | B1 | 8/2003 | Amid et al. |
| 6,610,088 | B1 | 8/2003 | Gabbay |
| 6,638,284 | B1 | 10/2003 | Rousseau et al. |
| 6,652,595 | B1 | 11/2003 | Nicolo |
| 6,669,735 | B1 * | 12/2003 | Pelissier .................... 623/23.74 |
| 2001/0027347 | A1 | 10/2001 | Rousseau |
| 2001/0049539 | A1 | 12/2001 | Rehil |
| 2002/0082707 | A1 | 6/2002 | Homsy |
| 2002/0103494 | A1 | 8/2002 | Pacey |
| 2002/0147457 | A1 | 10/2002 | Rousseau |
| 2002/0173804 | A1 | 11/2002 | Rousseau |
| 2002/0188350 | A1 | 12/2002 | Arru |
| 2003/0004581 | A1 | 1/2003 | Rousseau |
| 2003/0078602 | A1 | 4/2003 | Rousseau |
| 2003/0130745 | A1 * | 7/2003 | Cherok et al. ............. 623/23.72 |
| 2003/0181988 | A1 | 9/2003 | Rousseau |
| 2003/0191538 | A1 | 10/2003 | Buckberg et al. |
| 2004/0087980 | A1 | 5/2004 | Ford et al. |

FOREIGN PATENT DOCUMENTS

| | | |
|---|---|---|
| FR | 2 735 353 A1 | 12/1996 |
| FR | 2 778 554 A1 | 11/1999 |
| WO | WO 92/06639 A2 | 4/1992 |
| WO | WO 94/17747 A1 | 8/1994 |
| WO | WO 95/32687 A1 | 12/1995 |
| WO | WO 96/09795 A1 | 4/1996 |
| WO | WO 96/14805 A1 | 5/1996 |
| WO | WO 96/41588 A1 | 12/1996 |
| WO | WO 97/22310 A2 | 6/1997 |
| WO | WO 99/03422 A1 | 1/1999 |
| WO | WO 99/13802 A1 | 3/1999 |
| WO | WO 99/20204 A1 | 4/1999 |
| WO | WO 00/07520 A1 | 2/2000 |
| WO | WO 02/22047 A1 | 3/2002 |
| WO | WO 02/087468 A1 | 11/2002 |
| WO | WO 02/091953 A1 | 11/2002 |
| WO | WO 03/002029 A1 | 1/2003 |
| WO | WO 03/034950 A1 | 5/2003 |

* cited by examiner

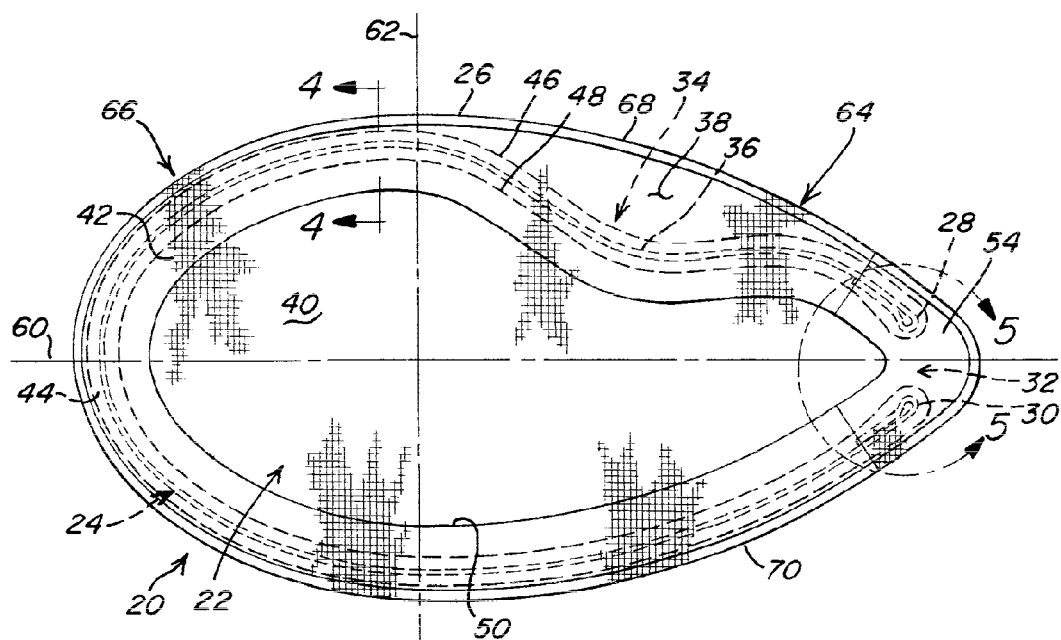
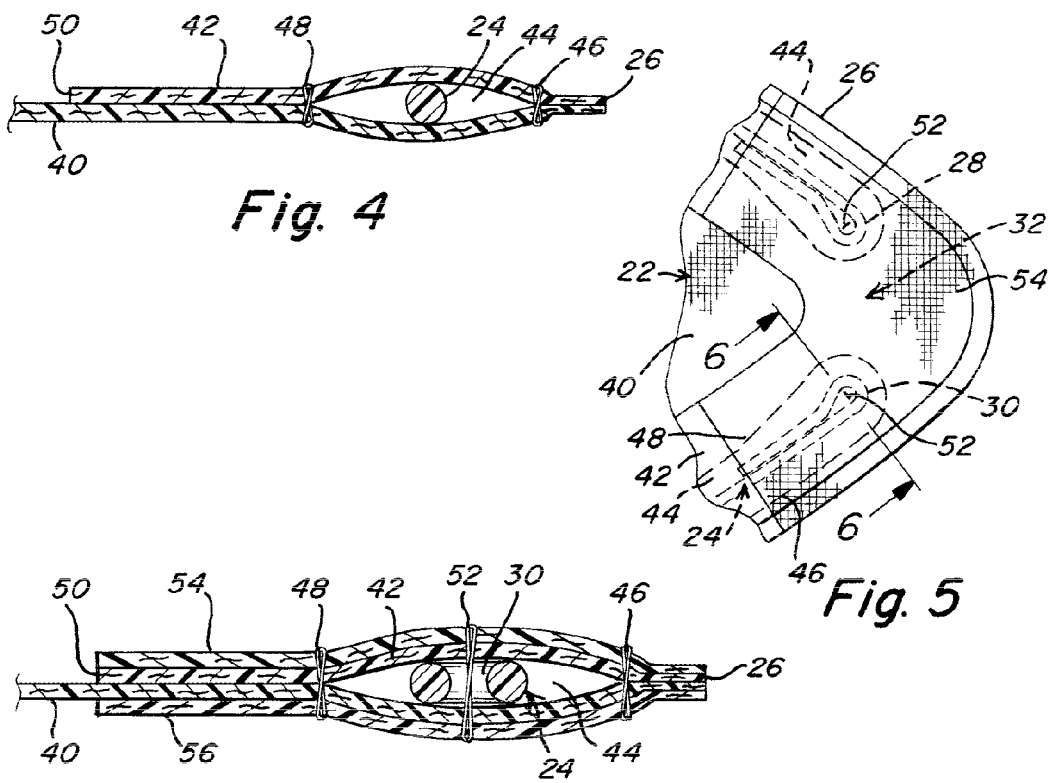
Fig. 1
Fig. 4
Fig. 5
Fig. 6

IMPLANTABLE PROSTHESIS FOR SOFT TISSUE REPAIR

BACKGROUND OF INVENTION

1. Field of Invention

The present invention relates to an implantable prosthesis, and more particularly, to a prosthesis for repairing or augmenting defects and/or weaknesses in a soft tissue or muscle wall.

2. Discussion of Related Art

Various prosthetic repair materials are known for repairing and reinforcing anatomical defects, such as soft tissue and muscle wall hernias. For example, ventral and inguinal hernias are commonly repaired using a sheet of biocompatible fabric, such as a knitted polypropylene mesh (e.g., BARD MESH). Once inserted into a patient, the fabric is typically sutured, stapled, tacked or otherwise provisionally anchored in place over, under or within the defect. Tissue integration with the fabric, such as by tissue ingrowth into the fabric, eventually completes the repair.

For an inguinal hernia repair, the mesh fabric may be trimmed, as necessary, to match the particular size and shape of the inguinal floor. A slit may be preformed or made by a surgeon from the lateral end of the mesh opposite the medial corner of the inguinal canal toward the medial end of the mesh to form a pair of lateral tails that are separated to receive the spermatic cord therebetween. The tails may then be overlapped to encircle the cord and reinforce the internal ring. A preshaped mesh may be provided with the slit and a keyhole at the end of the slit for receiving the cord therein.

It is an object of the present invention to provide a method and prosthesis for repairing and reinforcing soft tissue and muscle walls.

SUMMARY OF INVENTION

The present invention relates to an implantable prosthesis for repairing an anatomical defect, such as a tissue or muscle wall hernia, including an inguinal hernia.

In one embodiment, an implantable prosthesis is provided for repairing a tissue or muscle wall defect near a body structure. The implantable prosthesis comprises a patch of repair fabric including a body portion that is constructed and arranged to cover at least a portion of the tissue or muscle wall defect. The prosthesis also comprises a member that substantially surrounds the body portion of the patch. The support member includes opposing ends that are spaced apart to form an interruption. The support member further includes an indentation extending along a portion thereof that is adapted to be positioned adjacent the body structure.

In another embodiment, an implantable prosthesis is provided for repairing an existing or potential tissue or muscle wall defect near a body structure. The implantable prosthesis comprises a patch of repair fabric including a body portion that is constructed and arranged to cover at least a portion of the tissue or muscle wall defect. The patch has a non-circular shape with a major axis and a minor axis. The prosthesis also comprises a member that substantially surrounds the body portion of the patch. The member includes an indentation extending along a portion thereof that is adapted to be positioned adjacent the body structure. The indentation is offset from the minor axis of the patch.

In yet another embodiment, an implantable prosthesis is provided for repairing an existing or potential tissue or muscle wall defect near a body structure. The implantable prosthesis comprises a patch of repair fabric including a body portion that is constructed and arranged to cover at least a portion of the tissue or muscle wall defect. The prosthesis also comprises a member that substantially surrounds the body portion of the patch. The support member includes a single indentation extending along a portion thereof that is adapted to be positioned adjacent the body structure.

In a further embodiment, an implantable prosthesis is provided for repairing an existing or potential tissue or muscle wall defect. The implantable prosthesis comprises a patch of repair fabric including a body portion that is constructed and arranged to cover at least a portion of the tissue or muscle wall defect. The prosthesis also comprises a member that substantially surrounds the body portion of the patch. The support member includes opposing ends that are spaced apart to form an interruption. At least one of the repair fabric and the opposing ends of the support member is constructed and arranged to inhibit the opposing ends from protruding through the repair fabric.

In another embodiment, an implantable prosthesis is provided for repairing an inguinal hernia near the spermatic cord and femoral vessels. The implantable prosthesis comprises a patch of repair fabric including a body portion that is constructed and arranged to cover at least a portion of the inguinal hernia in a spread out configuration.

The prosthesis also comprises a ring-like member that substantially surrounds the body portion of the patch to help deploy and/or hold the body portion in the spread out configuration. The ring-like member includes an interruption that is constructed and arranged to allow passage of the spermatic cord therethrough and into an interior region of the body portion. The ring-like member further includes an indentation that is constructed and arranged to receive the femoral vessels when the body portion is covering the inguinal hernia. The interruption is located at a region of the patch spaced away from the indentation.

In a further embodiment, a method is provided to repair a tissue or muscle wall defect near a body structure. The method comprises providing an implantable prosthesis including a patch of repair fabric including a body portion that is constructed and arranged to cover at least a portion of the tissue or muscle wall defect in a spread out configuration. The prosthesis further includes a member substantially surrounding the body portion of the patch to help deploy and/or hold the body portion in the spread out configuration. The member includes opposing ends that are spaced apart to form an interruption. The member further includes an indentation extending along a portion thereof that is adapted to be positioned adjacent the body structure. The method also comprises implanting the prosthesis at the tissue or muscle wall defect with the body portion covering at least a portion of the tissue or muscle wall defect; and positioning the indentation adjacent the body structure.

In another embodiment, a method is provided to repair a tissue or muscle wall defect near a body structure. The method comprises providing an implantable prosthesis including a patch of repair fabric having a body portion that is constructed and arranged to cover at least a portion of the tissue or muscle wall defect in a spread out configuration. The prosthesis further includes a member substantially surrounding the body portion of the patch to help deploy and/or hold the body portion in the spread out configuration. The member including first and second ends that are spaced apart to form an interruption. At least one of the repair fabric and the first and second ends of the member being constructed and arranged to inhibit the first and second ends from protruding through the repair fabric. The method also comprises forming a slit in the repair fabric which extends through the interruption between the first and second ends and into the body portion; implanting the prosthesis at the tissue or muscle wall defect with the body portion covering at least a portion of the tissue or muscle wall defect; and placing the body structure through the slit.

Various embodiments of the present invention may provide certain advantages and may overcome certain drawbacks of prior prostheses. Embodiments of the invention may not share the same advantages, and those that do may not share them under all circumstances.

BRIEF DESCRIPTION OF DRAWINGS

Various embodiments of the invention will now be described, by way of example, with reference to the accompanying drawings, in which:

FIG. 1 is a plan view of an implantable prosthesis for soft tissue repair according to one illustrative embodiment;

FIG. 4 is a cross sectional view taken along section line 4-4 of FIGS. 1 and 3;

FIG. 5 is an enlarged view of an end portion of the implantable prosthesis of FIG. 1 illustrating the interruption and ends of the support member;

FIG. 6 is a cross sectional view taken along section line 6-6 of FIG 5. 5; and

DETAILED DESCRIPTION

Figure 2:
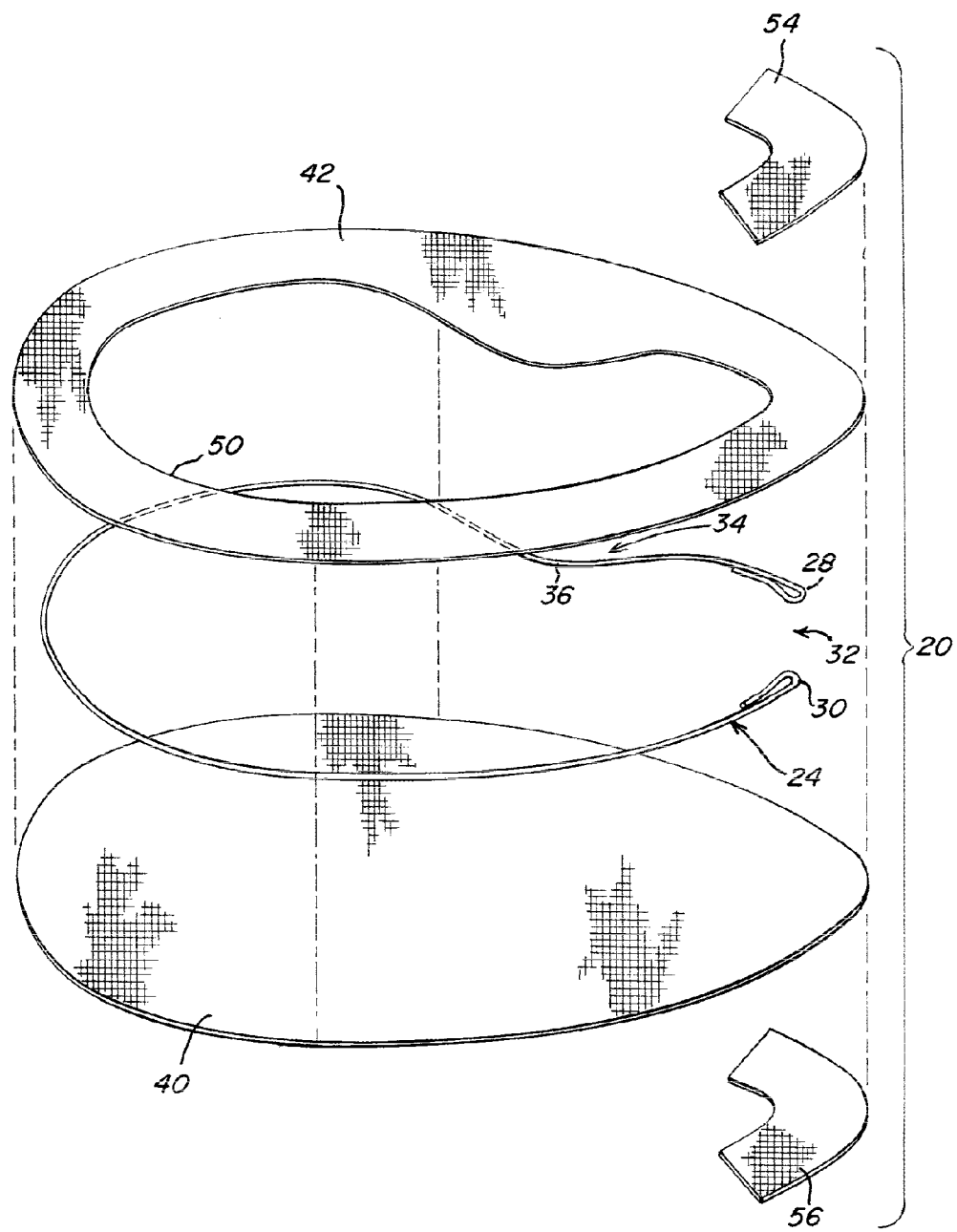
FIG. 2 is an exploded perspective view of the implantable prosthesis of FIG. 1.

The invention is directed to an implantable prosthesis for repairing or augmenting anatomical defects, and is particularly suitable for the repair of defects in, and weaknesses of, soft tissue and muscle walls or other anatomical regions. For ease of understanding, and without limiting the scope of the invention, the prosthesis is described below particularly in connection with the repair of an inguinal hernia. It should be understood, however, that the prosthesis is not so limited and may be employed in other anatomical procedures, as would be apparent to one of skill in the art.

The invention is more particularly directed to a prosthesis that includes a repair fabric having a body portion that is larger than at least a portion of the defect or weakness so that placement of the body portion against the defect will cover or extend across that portion of the opening or weakness. The prosthesis further includes a member, such as a support member, that may be arranged in or on the repair fabric to help deploy the repair fabric at the surgical site and/or help inhibit folding or buckling of the repair fabric.

The support member may substantially surround the body portion, such as in a ring-like manner, to help deploy and/or hold the body portion in an open or spread out configuration for covering the defect. The support member may have a resiliency that allows the support member to deform from an initial shape and then return to the initial shape to return the body portion of the patch to the spread out configuration. The support member may include first and second ends that are spaced apart to form an interruption. In this manner, a slit, such as a keyhole arrangement, may be readily formed in the repair fabric through the interruption and into an interior region of the body portion. The slit and/or keyhole may be configured to receive a body structure, including a cord structure such as the spermatic cord. It is to be understood, however, that the support member may be configured to completely surround the body portion and not include an interruption.

The support member may be configured to generally follow the shape of the outer periphery of the repair fabric about the body portion. A portion of the support member may deviate inwardly toward the body portion to form an indentation or notch that is adapted to be positioned adjacent to a body structure, such as the femoral vessels during an inguinal hernia repair procedure. A portion of the repair fabric may extend across the indentation or notch between the support member and the outer periphery. Alternatively, the prosthesis may be configured with the outer periphery of the repair fabric following the shape of the support member indentation so that the indentation or notch is substantially free of repair fabric material.

The support member may include a single indentation or notch that is located at a specific region of the prosthesis to accommodate a particular structure at the repair site. The indentation may be located at a region of the repair fabric that will be positioned adjacent the femoral vessels of a patient during an inguinal hernia repair so that these vessels are received within the indentation. In this manner, the support member is configured to avoid the femoral vessels.

The prosthesis may have a non-circular shape, such as a generally oval, elliptical or egg shape, that is suitable for augmenting or repairing an inguinal hernia. The prosthesis may be shaped so as to have a major axis and a minor axis. The support member may include an indentation or notch that is offset to one side of the minor axis of the prosthesis for accommodating a body structure, such as the femoral vessels. The prosthesis may be generally symmetric about its major axis and generally asymmetric about its minor axis.

The support member may be sandwiched between two layers of fabric material. To reduce the amount of material employed for the prosthesis, one of the fabric layers may have a generally annular configuration that follows and overlies the support member. The support member and/or the repair fabric may be configured so as to inhibit protrusion of the ends of the support member through the fabric in the vicinity of the interruption. In this regard, the ends of the support member may include an enlarged head or tip, the ends of the support member may be restrained against movement, and/or the repair fabric may be reinforced about the ends of the support member.

The support member may be rollable, foldable or otherwise collapsible, when the repair fabric is reduced in size for delivery to the repair site, and may spring back, either automatically or upon the influence of a force (e.g., body heat where the support is formed of a shape memory material, such as NITINOL) to its initial expanded shape on deployment at the repair site, influencing the prosthesis to assume its unfurled or spread out configuration.

The repair fabric may be formed of a tissue infiltratable material, such as a knit fabric, or may be composed of a solid or substantially non-porous material. The repair fabric may be formed of one or more layers of the same or dissimilar material. The repair fabric may be formed with portions that are tissue infiltratable and other portions that are non-tissue infiltratable, providing selected areas of the repair device with different tissue ingrowth and adhesion resistant properties. The repair fabric may be formed of permanent or resorbable material.

The support member may be formed of a monofilament that has been preformed into the desired shape. The support member may be comprised of a non-resorbable or a resorbable material.

The prosthesis may be placed at the defect site using an open surgical procedure, or by laparoscopically passing the device through a cannula to the defect. The repair fabric may be flexible, allowing reduction of the prosthesis, such as by folding, rolling or otherwise collapsing the repair fabric, into a slender configuration suitable for delivery to the defect site. Upon delivery, the repair fabric may automatically open to an unfurled or spread out configuration, or may be unfolded, unrolled or otherwise deployed by the surgeon to an unfurled or spread out configuration suitable to repair the weakness or defect.

FIGS. 1-2 illustrate one embodiment of a prosthesis 20 for repairing or augmenting soft tissue and muscle wall defects, such as an inguinal hernia.

The prosthesis 20 includes a repair fabric of implantable, biologically compatible material with a body portion 22 that is configured to cover at least a portion of the defect. As shown, the prosthesis is configured as a patch that may be used as an underlay or an overlay. The prosthesis may be configured with any desired strength, flexibility, tissue integration, adhesion resistance and/or other characteristics suitable for the repair as would be apparent to one of skill. Although the prosthesis is described in connection with a patch-type embodiment, the prosthesis may include a plug, a combination plug and patch, and other suitable arrangements for mending the defect.

To help deploy the patch into a spread out configuration for covering a defect or weakness, it may be desirable to employ a patch that is sufficiently rigid so that it can be easily and effectively manipulated and positioned in the desired area, yet sufficiently flexible so that the patch may be adequately handled by the physician implanting the patch and tolerated by the patient receiving the patch. In one illustrative embodiment as shown in FIGS. 1-2, to balance the stiffness and flexibility characteristics, the prosthesis 20 includes a support member 24 to reinforce portions of the patch and to help deploy and/or hold the patch in a spread out configuration. The support member 24 may be coupled to the patch in any suitable manner, as the present invention is not limited in this respect. Suitable attachment methods include, but are not limited to, stitching, bonding, adhesive, and integral formation with the repair fabric of the patch, as will be discussed further below.

The support member 24 contributes to the stability of the patch, allowing it to deploy into and remain in a desired shape. For example, the support member may aid in returning the patch to a substantially unfurled or spread out configuration after the folded up or otherwise reduced prosthesis has been delivered to the repair site through either an open incision or a cannula. This stability facilitates deployment and placement of the patch by making it easy to handle. Also, this stability minimizes the tendency of the patch to fold, bend, or otherwise be dislocated. Difficulty in handling, dislocation or bending could require additional operative procedures and/or additional anchoring during implantation.

In one embodiment, the support member includes a substantially continuous loop or ring positioned adjacent the outer margin of the patch. In the illustrative embodiment, the support member 24 is spaced inwardly from the outer peripheral edge 26 of the repair fabric. However, it should be appreciated that the present invention is not limited in this respect, as the support member 24 may be disposed at the peripheral edge and/or at discrete locations throughout the body of the patch.

The support member 24 may be configured to substantially surround the body portion so as to help deploy and/or hold the body portion 22 in the spread out configuration for covering the defect. The support member 24 may have a resiliency that allows the support member to deform from an initial shape and then return to the initial shape to return the body portion to the spread out configuration.

As illustrated, the support member 24 may include first and second ends 28, 30 that are spaced apart to form an interruption 32 in the support member at one end of the prosthesis. In this manner, a slit and/or keyhole arrangement may be readily formed in the repair fabric at the interruption 32 and into an interior region of the body portion 22 without having to cut through the support member. The slit and/or opening may be configured to receive a body structure, including a cord structure such as the spermatic cord. It is to be understood, however, that the support member may be configured to completely surround the body portion and not include an interruption.

In certain repair procedures, it may be desirable to configure the support member so as to accommodate a particular body structure at the repair site. In one embodiment, the support member may be configured to avoid the femoral vessels during an inguinal hernia repair.

In one illustrative embodiment shown in FIGS. 1-2, the support member 24 may include an indentation or notch 34 that is configured to accommodate the particular body structure. As shown, a portion 36 of the support member 24 may deviate inwardly away from the outer periphery 26 of the patch to form the indentation. The overall support member 24 may have a generally convex curvature as it extends about the body portion 22 while the portion 36 of the support member forming the indentation 34 may have a generally concave curvature. In this manner, the indentation 34 may have a curved shape that extends about the body structure when the prosthesis is implanted at the defect site.

In the illustrative embodiment shown in FIG. 1, a segment 38 of repair fabric may occupy the region of the patch at the indentation 34 between the support member 24 and the outer periphery 26. In some instances, a surgeon may wish to retain this segment 38 of repair fabric on the prosthesis for the repair procedure. For example, a surgeon may find it desirable to enhance tissue ingrowth in the vicinity of the femoral vessels in an inguinal hernia repair. In other instances, a surgeon may find it desirable to remove this segment of the repair fabric from the prosthesis.

Figure 3:
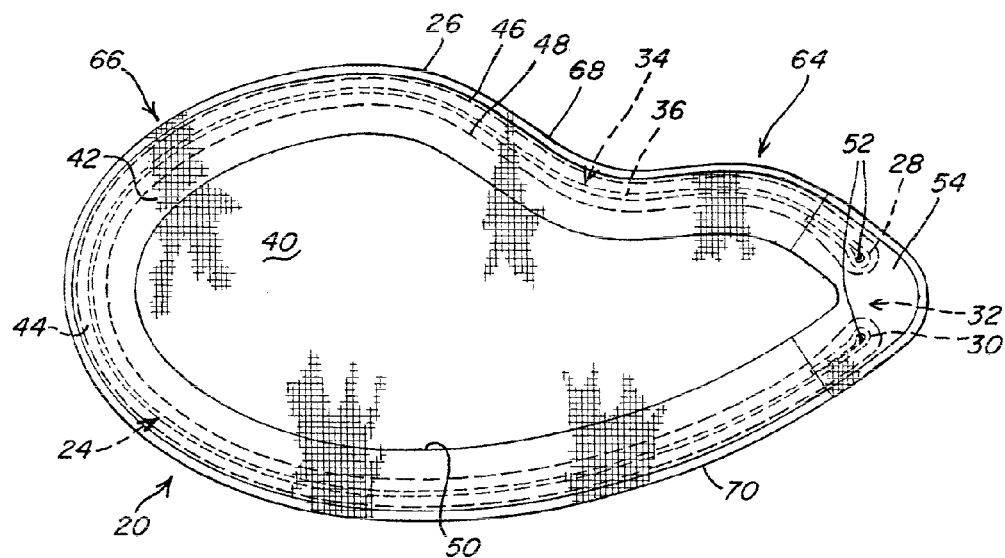
FIG. 3 is a plan view of an implantable prosthesis for soft tissue repair according to another illustrative embodiment.

In an illustrative embodiment shown in FIG. 3, the prosthesis 20 may be constructed so that the outer periphery 26 of the patch follows the contour of the support member 24 at the indentation 34 so that excess fabric material would not need to be removed by the surgeon.

In the illustrative embodiments shown in FIGS. 1-3, the support member 24 includes a single indentation 34 for accommodating a body structure during a repair procedure. However, it is to be appreciated that two or more indentations may be provided so as to accommodate multiple structures in the repair site. Additionally, the support member may include a pair of indentations that are symmetrically positioned on the patch so that the prosthesis may be readily employed for various repairs, such as left and right side inguinal hernia repairs. However, it is to be understood that multiple indentations are not required to employ the prosthesis for repairing both left side and right side inguinal hernias. As one of ordinary skill in the art would appreciate, a prosthesis with a single indentation 34, such as the prosthesis 20 shown in FIGS. 1-3, may be employed for both left side and right side inguinal hernia repairs by turning over the prosthesis.

The support member 24 may be disposed on the patch in any suitable manner as the present invention is not limited in this respect. In one embodiment, as shown in FIGS. 1-4, the support member 24 is sandwiched between first and second layers 40, 42 of repair fabric and may or may not be physically attached thereto. The support member 24 may be tightly or loosely held within a channel 44 between the first and second layers 40, 42 and formed by a pair of seams 46, 48 joining the first and second layers. In the illustrative embodiment, the channel 44 is formed by a pair of seams 46, 48 that follow the contour of the support member 24. The seams 46, 48 may be formed by a series of stitches extending along the outside and inside edge of the support member 24 to keep it from moving with respect to the first and second layers 40, 42. Because of the rigidity of the support member 24, one seam extending along one side of the support member may be sufficient.

It should be appreciated that the invention is not limited to any particular attachment method, as the first and second layers 40, 42 may be attached along the seams 46, 48 or other desired locations using other suitable techniques. For example, the layers may be bonded together by melting the layers at specific locations or in a specific pattern; sonic, induction, vibration, or infrared/laser welding the layers; or using a suitable bonding agent. The point or points of attachment may comprise any suitable pattern as would be apparent to one of skill in the art.

Alternatively, rather than being sandwiched between the first and second layers, the support member 24 may overlie or underlie the repair fabric and may be attached, regardless of location, with stitches or a bonding agent, or fused with ultrasonic, induction, vibration, infrared/laser welding and the like. Alternatively, the support member 24 may be woven through at least one of the layers or integrally formed with one or both layers during fabrication of the layer itself.

In one illustrative embodiment shown in FIGS. 1-3, the first layer 40 may be configured as a full layer of fabric material that is sized and shaped to cover the defect. The second layer 42 may have a generally annular configuration that overlies and generally follows the contour of the support member to reduce the overall amount of material for the prosthesis. As shown, the second layer 42 has an inner edge 50 that is configured to follow the contour of the support member. However, it is to be appreciated that the second layer 42 may be configured as a full layer of fabric material that corresponds to the first layer 40. Such an arrangement may provide additional strength and/or tissue ingrowth if desired by a surgeon. Such an arrangement may also provide for the formation of a pocket between the layers that may aid in deploying and/or positioning of the prosthesis during implantation as would be understood by one of skill in the art.

In some instances, it may be desirable to inhibit protrusion of the ends of the support member through the repair fabric of the patch. In this regard, the repair fabric and/or the support member may be constructed to resist protrusion and retain the ends of the support member within the repair fabric.

In one illustrative embodiment, the ends 28, 30 of the support member 24 may include an enlarged head having a configuration or size which exceeds the pore size of the fabric to reduce the likelihood that the head may protrude through the pores of the fabric. As shown in FIGS. 1-3 and 5, a loop may be formed at each end 28, 30 of the support member 24 with a size that exceeds the pore size of the fabric. The loop may also aid to distribute forces that could potentially be exerted against the fabric by the ends of the support member to help reduce the potential that the ends could puncture through the fabric. In one embodiment, the loop may be formed by bending a length of the support member back onto itself and then joining the looped portion to the main body of the support member. It is to be appreciated that the ends of the support member may employ any suitable configuration formed using any suitable techniques apparent to one of skill in the art to inhibit protrusion of the ends from the fabric.

In addition to or in place of an enlarged head at the ends of the support member, the support member may be anchored to the repair fabric in a manner that restrains movement of the support member so as to inhibit the ends from protruding from the fabric. In one illustrative embodiment shown in FIGS. 5-6, each end 28, 30 of the support member may be attached to the repair fabric in a manner that restrains movement of the ends relative to the fabric. As shown, each loop may be staked to the fabric with one or more stitches 52 that extend through the loop and join the fabric layers 40, 42 to each other to restrain movement of the loop. It is to be appreciated that any suitable arrangement apparent to one of skill in the art may be implemented to restrain movement of the looped ends. For example, the layers 40, 42 of fabric may be ultrasonically welded, melted, mechanically fastened or bonded to each other within the looped ends 28, 30 of the support member.

It may be desirable to reinforce the repair fabric adjacent the ends of the support member to reduce the potential for the ends to puncture or protrude through the fabric. In one illustrative embodiment shown in FIGS. 1-3 and 5-6, first and second reinforcement layers 54, 56 of fabric material may be added to the patch in the vicinity of the interruption 34. The reinforcement layers 54, 56 are configured to overlie portions of the first and second layers 40, 42 of fabric with the outer and inner seams 46, 48 extending about the looped ends 28, 30 and joining all of the layers to each other. In this manner, a reinforced pocket is formed about each end 28, 30 of the support member to further reduce the potential for the ends to protrude through or puncture the repair fabric. Rather, than overlying the first and second layers, it is to be appreciated that the reinforcement layers may be sandwiched between the first and second layers.

Although the illustrative embodiments of the prostheses shown in FIGS. 1-3 and 5-6 employ multiple features to inhibit protrusion of the ends 28, 30 of the support member 24, it is to be appreciated that any one or combination of these or other suitable features apparent to one of skill in the art to inhibit protrusion of the ends may be implemented in the prosthesis. It is also to be understood that a prosthesis may not need any feature to inhibit protrusion of the ends of the support member and that the prosthesis is not so limited in this regard.

The prosthesis may be configured to have any suitable shape or size that is conducive to facilitating the correction or repair of a particular defect, such as an inguinal hernia. In the embodiments shown in FIGS. 1-3, the patch has a relatively flat configuration. However, the patch need not be flat, and convex, concave, convex/concave, and more complex three-dimensional shapes also are contemplated. The patch may be pliable to facilitate manipulation and/or reduction of the patch during delivery to the defect and/or to conform the patch to the anatomical site of interest.

In the illustrative embodiments shown in FIGS. 1-3, the prosthesis has a generally oval, elliptical or egg shape suitable for augmenting or repairing an inguinal hernia in the inguinal canal. The geometry of the prosthesis 20 is generally elliptical with a major axis 60 extending along the longest portion of the prosthesis and a minor axis 62 extending across the widest portion of the prosthesis in a direction perpendicular to the major axis. As illustrated in FIG. 1, the prosthesis is substantially symmetric about the major axis 60 and is substantially asymmetric about the minor axis 62, providing a generally ellipsoid shape (e.g., egg shape) with a narrower or acute end 64, a wider or obtuse end 66, and opposing sides 68, 70 that converge towards each other in a direction from the obtuse end 66 toward the acute end 64. It is to be appreciated that the prosthesis may be configured with any suitable shape, such as a shape that is symmetric about both axes, asymmetric about both axes, or asymmetric about the major axis and symmetric about the minor axis. Examples of other shapes include, but are not limited to, circular, square, rectangular, and irregular configurations. The repair fabric may be sized to cover part or, preferably, all of the defect.

The obtuse end 66 has a rounded configuration that generally conforms to the shape of the repair site, such as the medial corner of the inguinal canal. The obtuse end 66 is configured to overlie and cover the defect. The acute end 64 of the prosthesis is configured to generally be positioned at the repair site away from the defect. Therefore, the acute end may have a smaller configuration relative to the obtuse end to reduce the overall amount of material introduced by the prosthesis during a repair procedure. However, it is to be understood that the obtuse end and the acute end may have any suitable configurations apparent to one of skill in the art.

The interruption 32 and the indentation 34 may be positioned in any desirable location, relative to the body portion 22, that is suitable for a particular repair. In the illustrative embodiment, the interruption 32 is centrally located along the major axis 60 at the acute end 64 of the prosthesis. The indentation 34 is positioned offset from the minor axis 62 toward the acute end 64 of the prosthesis. As shown, the indentation 34 may be located entirely to one side of the minor axis toward the acute end. The illustrated embodiments of the interruption and the indentation are particularly suited for repair of an inguinal hernia. However, it is to be appreciated that the prosthesis is not so limited and the locations of the interruption and/or the indentation may be varied for other repairs as would be apparent to one of skill in the art.

As indicated above, the prosthesis 20 may be used in the repair of an inguinal hernia. More particularly, the prosthesis illustrated in FIGS. 1-3 is particularly suited for a direct inguinal hernia. The obtuse end of the body portion 22 is configured to be placed over the hernia defect and the indentation 34 is configured to be positioned adjacent the femoral vessels. As indicated above, the segment 38 of repair fabric (FIG. 1) may be retained for the repair or removed (FIG. 3) as desired by a surgeon.

Figure 7:
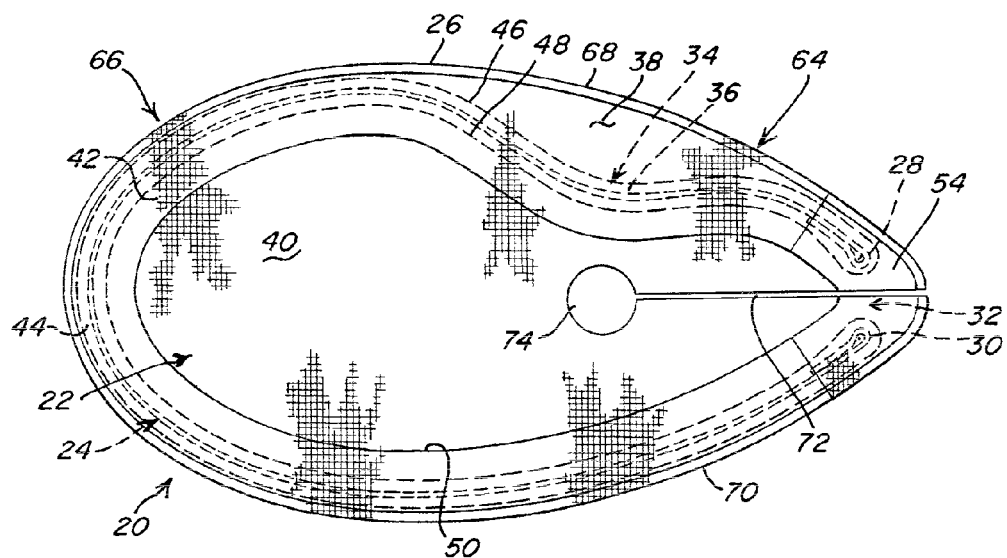
FIG. 7 is a plan view of an implantable prosthesis for soft tissue repair according to a further illustrative embodiment illustrating a slit and keyhole arrangement.

For repair of an indirect hernia repair, the prosthesis may be provided with a slit and/or keyhole arrangement to accommodate the spermatic cord upon placement of the prosthesis at the repair site. In one illustrative embodiment shown in FIG. 7, a slit 72 extends inwardly from the outer peripheral edge 26 of the repair fabric through the interruption 32 and into a region of the body portion adjacent the indentation 34. A keyhole opening 74 for receiving the spermatic cord may be formed at the end of a slit. However, it is to be understood that the keyhole opening is not required and the slit alone may be provided for receiving the cord. The slit 72 creates a pair of tails at the acute end of the prosthesis that may be separated to receive the spermatic cord in an inguinal hernia repair. However, it should be recognized that the prosthesis may be configured to have any suitable shape that is conducive to facilitating repair of a particular defect.

The slit 72 and/or keyhole opening 74 may be pre-formed into the prosthesis or formed by a surgeon during the repair procedure. The interruption 32 allows the slit to be readily cut in the repair fabric.

In one embodiment for an inguinal hernia repair, the prosthesis 20 has a length along the major axis 60 of approximately 6.29 inches and a width along the minor axis 62 of approximately 3.73 inches. The interruption may have a width from approximately 0.5 cm to approximately 4.0 cm. However, it is to be understood that these dimensions are merely exemplary and that the prosthesis may be configured to have any suitable size and interruption width as would be apparent to one of skill for a particular repair.

The repair fabric may include at least one layer of tissue infiltratable material that permits or is otherwise susceptible to tissue or muscle ingrowth to enhance the repair of the defect. In one embodiment, each of the first and second layers 40, 42 and the reinforcement layers 54, 56 is formed of a biologically compatible, flexible repair material that includes a plurality of interstices or openings which allow sufficient tissue or muscle ingrowth to integrate the prosthesis with host tissue or muscle after implantation. Multiple layers of tissue infiltratable fabric may enhance the strength of the patch and/or the amount of tissue ingrowth to the patch. Preferably, the first and second layers and the reinforcement layers are formed of the same tissue infiltratable material. However, the invention is not limited in this respect, and any one or each layer may be formed of any biologically compatible material, suitable for repairing a tissue or muscle wall defect as would be apparent to one of skill.

In one embodiment, the first and second layers 40, 42 and the reinforcement layers 54, 56 the prosthesis 20 are each formed from a sheet of knitted polypropylene monofilament mesh fabric having a thickness of approximately 0.014 inches and knitted from polypropylene monofilament having a diameter of approximately 0.0042 inches. When implanted, the polypropylene mesh promotes rapid tissue or muscle ingrowth into and around the mesh structure. Alternatively, other surgical materials which are suitable for tissue or muscle reinforcement and defect correction may be utilized including BARD MESH (available from C. R. Bard, Inc.), SOFT TISSUE PATCH (microporous ePTFE—available from W. L. Gore & Associates, Inc.); SURGIPRO (available from US Surgical, Inc.); TRELEX (available from Meadox Medical); PROLENE and MERSILENE (available from Ethicon, Inc.); and other mesh materials (e.g., available from Atrium Medical Corporation). Resorbable materials, including polyglactin (VICRYL—available from Ethicon, Inc.) and polyglycolic acid (DEXON—available from US Surgical, Inc.), may be suitable for applications involving temporary correction of tissue or muscle defects. Collagen materials such as COOK SURGISIS, available from Cook Biomedical, Inc. may also be used. It also is contemplated that the mesh fabric may be formed from multifilament yarns and that any suitable method, such as knitting, weaving, braiding, molding and the like, may be employed to form the mesh material.

In the embodiments shown, the support member 24 includes a monofilament of a desired thickness and cross-sectional shape to provide a desired degree of resilience or rigidity. It should be appreciated that the support member may have any cross-sectional shape, such as circular, square, rectangular, triangular, elliptical, etc. The support member may be configured on the patch in any pattern, such as a spiral pattern, a square pattern, an elliptical pattern, a circular pattern, crisscross pattern or the like.

The support member may be formed of a non-resorbable or resorbable material as desired for the particular repair procedure. In one embodiment, the support member may be formed of a non-resorbable material comprised of polyethylene terephthalate (PET). In another embodiment, the support member may be formed of a resorbable material comprised of a 70/30 blend of polylactic acid (PLA) and polycaprolactone (PCL). However, it is to be appreciated that the support member may be fabricated from any suitable material apparent to one of skill in the art to provide the desired properties for the support member.

The stiffness or rigidity of the support member may be varied depending on the size of the patch. For example, the cross-sectional diameter and/or the spring constant of the material of the monofilament may be varied in a manner to provide a desired stiffness.

In one embodiment, the support member may be formed from a length of 0.042 inch diameter non-resorbable polyethylene terephthalate (PET) monofilament. In another embodiment, the support member may be formed from a length of 0.055 inch diameter resorbable PLA/PCL blend monofilament. However, it should be appreciated that the invention is not limited in this respect and that the support member may be made of any suitable non-resorbable and resorbable material including nylon, polypropylene, and polyester and having any suitable diameter or cross-section.

Although the support member 24 is described as being formed of a monofilament, other suitable constructions may be employed. For example, the support member may be molded elements that are subsequently attached to the patch or molded onto the patch. As another example, the support member may be formed from the repair fabric. In this respect, the support member may be formed by melting a portion of the repair fabric in any desired shape. In another example, the support member may be formed by multiple stitches passing through one or more layers, such as, for example, an embroidered section. Alternatively, the support member may be formed by altering the weave pattern in a zone of desired reinforcement. In this manner, the area of the repair fabric where tissue ingrowth may be desired may be formed with a relatively loose open weave, whereas the area or zone of reinforcement may be formed with a relatively tight weave, to provide the desired rigidity. Other suitable methods or mechanisms to form the support member may be employed, as the present invention is not limited in this respect.

In one embodiment, the fabric layers may be attached using stitches formed with a suitable polytetrafluoroethylene (PTFE) monofilament having a diameter of approximately 0.010 inches. The PTFE stitches may provide a softer, more flexible prosthesis that is easier to manipulate as compared to a prosthesis using other stitch materials, such as polypropylene monofilament. PTFE monofilament also facilitates the manufacturing process due to the low friction characteristics of the material. Nevertheless, it should be understood that any suitable material, such as polypropylene monofilament, may be employed for the stitches.

In one embodiment, the first or outer stitch line 46 is placed approximately 0.10 inches in from the peripheral edge of the layers of repair fabric. The second or inner stitch line 48 is placed approximately 0.28 inches in from the peripheral edge of the layers. The support member 24 is held in the 0.18 inch channel formed between the first and second stitch lines 46, 48. The outer 0.07 inches of the peripheral margin of the first and second layers 40, 42 are heat sealed to supplement attachment of the first and second layers.

The fabric layers 40, 42, 54, 56 may be stitched using a typical sewing stitch formed by a sewing machine using a bobbin and sewing thread. The first and second stitches 46, 48 and the tack stitches 52 may be formed using a #10 ball-tipped needle. The fabric layers may be held by a frame during the sewing procedure on a computer controlled table that has been programmed with the desired stitch pattern.

In certain embodiments, the prosthesis may include an adhesion resistant barrier overlying at least a portion, and preferably all, of one side of the ingrowth layer and/or an edge barrier to isolate one or more edges of the patch from adjacent tissue, muscle or organs. The barrier layer and/or edge barrier may be formed of a material and/or with a structure that does not substantially stimulate and, in certain embodiments, may resist tissue, muscle or organ ingrowth and adhesion formation when implanted, thereby reducing the incidence of undesired postoperative adhesions between the ingrowth layer and adjacent tissue, muscle or organs. If desired, such a barrier layer and/or edge barrier may be formed from any suitable material or structure apparent to one of skill in the art, including, but not limited to, a sheet of expanded polytetrafluoroethylene (ePTFE) having a microporous pore structure that inhibits tissue ingrowth.

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. An implantable prosthesis for repairing a tissue or muscle wall defect near a body structure, the implantable prosthesis comprising:
   a patch of repair fabric including a body portion that is constructed and arranged to cover at least a portion of the tissue or muscle wall defect, the patch including an outer periphery and having an oval shape with a major axis and a minor axis, the patch including a first end and an opposite second end and a first side and a second side extending between the first and second ends, the major axis extending from the first end to the second end; and
   a member substantially surrounding the body portion of the patch, the member terminating in first and second free ends that are spaced apart to form an interruption located at one of the first and second ends of the patch, the member including an indentation that is adapted to be positioned adjacent the body structure, the indentation formed by a portion of the member deviating inwardly away from the outer periphery and toward the body portion, the indentation being spaced from the interruption and located along the first side or the second side of the patch, the indentation being offset from the minor axis in a direction toward the interruption.

2. The implantable prosthesis according to claim 1, wherein the indentation has a curved shape.

3. The implantable prosthesis according to claim 2, wherein the member has a convex shape along a substantial portion thereof and the indentation has a concave shape.

4. The implantable prosthesis according to claim 1, wherein the interruption is located along the major axis.

5. The implantable prosthesis according to claim 1, wherein the patch includes an obtuse end and an acute end, the obtuse end being larger than the acute end.

6. The implantable prosthesis according to claim 5, wherein the indentation is offset from the minor axis toward the acute end.

7. The implantable prosthesis according to claim 6, wherein the interruption is located at the acute end along the major axis.

8. The implantable prosthesis according to claim 7, wherein the interruption is centered about the major axis.

9. The implantable prosthesis according to claim 1, wherein at least one of the repair fabric and the first and second ends of the member is constructed and arranged to inhibit the first and second ends from protruding through the repair fabric.

10. The implantable prosthesis according to claim 1, wherein the body portion is constructed and arranged to cover at least a portion of the tissue or muscle wall defect in a spread out configuration.

11. The implantable prosthesis according to claim 10, wherein the member is constructed and arranged to help deploy and/or hold the body portion in the spread out configuration.

12. The implantable prosthesis according to claim 11, wherein the member has a resiliency that allows the member to deform from an initial shape and then return to the initial shape to return the body portion of the patch to the spread out configuration.

13. The implantable prosthesis according to claim 1, wherein the repair fabric includes a first layer and a second layer, the member being disposed between the first layer and the second layer.

14. The implantable prosthesis according to claim 13, wherein the member is disposed within a channel defined by an inner seam and an outer seam joining the first layer to the second layer.

15. The implantable prosthesis according to claim 13, wherein the first layer has a first shape and the second layer has a second shape that is different from the first shape.

16. The implantable prosthesis according to claim 15, wherein the second layer has a generally annular shape.

17. The implantable prosthesis according to claim 16, wherein the second layer includes an inner edge that follows the shape of the member.

18. The implantable prosthesis according to claim 1, wherein the repair fabric is susceptible to the formation of adhesions with tissue and organs.

19. The implantable prosthesis according to claim 1, wherein the repair fabric has a plurality of interstices that are constructed and arranged to allow tissue ingrowth.

20. The implantable prosthesis according to claim 19, wherein the repair fabric includes at least one layer of mesh fabric.

21. The implantable prosthesis according to claim 1, wherein the member includes a monofilament.

22. The implantable prosthesis according to claim 1, wherein the member includes a single indentation along the entire length thereof.

23. The implantable prosthesis according to claim 1, wherein the outer periphery of the patch is symmetric about the major axis and asymmetric about the minor axis.

24. The implantable prosthesis according to claim 1, wherein the portion of the member forming the indentation has a first end and a second end, and wherein the first end of the portion of the member is located a first distance from the major axis in a direction perpendicular to the major axis and the second end of the portion of the member is located a second distance from the major axis in a direction perpendicular to the major axis, the first distance being greater than the second distance such that the indentation is radially skewed relative to the minor axis.

* * * * *